(12) United States Patent
Danielpour et al.

(10) Patent No.: US 12,414,947 B2
(45) Date of Patent: Sep. 16, 2025

(54) USE OF FGFR INHIBITORS FOR TREATMENT OF IDIOPATHIC SHORT STATURE

(71) Applicants: CEDARS-SINAI MEDICAL CENTER, Los Angeles, CA (US); Children's Hospital Medical Center, Cincinnati, OH (US)

(72) Inventors: Moise Danielpour, Los Angeles, CA (US); Fataneh Majlessipour, Los Angeles, CA (US); Vivian Hwa, Cincinnati, OH (US)

(73) Assignees: Cedars-Sinai Medical Center, Los Angeles, CA (US); Children's Hospital Medical Center, Cincinnati, OH (US)

( * ) Notice: Subject to any disclaimer, the term of this patent is extended or adjusted under 35 U.S.C. 154(b) by 762 days.

(21) Appl. No.: 17/782,534

(22) PCT Filed: Dec. 9, 2020

(86) PCT No.: PCT/US2020/063979
§ 371 (c)(1),
(2) Date: Jun. 3, 2022

(87) PCT Pub. No.: WO2021/119108
PCT Pub. Date: Jun. 17, 2021

(65) Prior Publication Data
US 2023/0011935 A1    Jan. 12, 2023

Related U.S. Application Data

(60) Provisional application No. 62/945,713, filed on Dec. 9, 2019.

(51) Int. Cl.
*A61K 31/498* (2006.01)
*A61K 47/54* (2017.01)
*A61P 43/00* (2006.01)

(52) U.S. Cl.
CPC ............ *A61K 31/498* (2013.01); *A61K 47/54* (2017.08); *A61P 43/00* (2018.01)

(58) Field of Classification Search
CPC ............................. A61K 31/498; A61P 43/00
See application file for complete search history.

(56) References Cited

U.S. PATENT DOCUMENTS

| 10,028,955 B2 | 7/2018 | Kneissel et al. |
| 2015/0011560 A1 | 1/2015 | Legeai-Mallet |

FOREIGN PATENT DOCUMENTS

| WO | 2015108998 A2 | 7/2015 |
| WO | 2018045058 A1 | 3/2018 |
| WO | 2018141921 A1 | 8/2018 |
| WO | 2021119108 A1 | 12/2020 |

OTHER PUBLICATIONS

International Search Report and Written Opinion for PCT/US2020/063979, dated Mar. 12, 2021, 9 pages.
Wohrle et al., Pharmacological Inhibition of Fibroblast Growth Factor (FGF) Receptor Signaling Ameliorates FGF23-Mediated Hypophosphatemic Rickets, Journal of Bone and Mineral Research, 2013, vol. 28(4), pp. 899-911.
Saw et al., Metalloprotease inhibitor TIMP proteins control FGF-2 bioavailability and regulate skeletal growth, Journal of Cell Biology, 2019, vol. 218(9), pp. 3134-3152.

*Primary Examiner* — Sahar Javanmard
(74) *Attorney, Agent, or Firm* — Linda B. Huber; Nixon Peabody LLP

(57) ABSTRACT

The present invention describes methods for treating idiopathic short stature. Described herein are also methods of increasing a subject's height. The methods involve administering an effective amount of a pan FGFR inhibitor or a selective FGFR inhibitor to the subject. An example of an FGRF inhibitor used in the methods described herein is erdafitinib.

17 Claims, 10 Drawing Sheets

USE OF FGFR INHIBITORS FOR TREATMENT OF IDIOPATHIC SHORT STATURE

CROSS-REFERENCE TO RELATED APPLICATIONS

This application is a National Phase of International Application No. PCT/US2020/063979, filed Dec. 9, 2020, which designated the U.S. and that International Application was published under PCT Article 21(2) in English, which claims priority to and benefit of U.S. provisional patent application No. 62/945,713, filed Dec. 9, 2019, the entirety of which is hereby incorporated by reference.

STATEMENT REGARDING FEDERALLY SPONSORED RESEARCH OR DEVELOPMENT

This invention was made with Government support under Grant No. CA180886 awarded by National Institutes of Health. The Government has certain rights in the invention.

FIELD OF INVENTION

This invention relates to the treatment of idiopathic short stature in patients who do not have a mutation in the fibroblast growth factor receptor genes.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Idiopathic short stature is can be defined statistically as height less than 2 standard deviations (SD) of the age- and sex-matched population. A recent consensus statement on the diagnosis and treatment of children with idiopathic short stature defines ISS simply by height >2 SD below the corresponding mean height of a given age, sex, and population group without evidence of systemic, endocrine, nutritional, or chromosomal abnormalities, and normal stimulated growth hormone (GH) levels.

Existing therapy involved growth hormone therapy but is not very effective in children who have normal growth hormone. As such, there remains a need in the art for effective and alternative treatments for short stature.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method for treating short stature, comprising: administering a therapeutically effective amount of a FGFR inhibitor to a subject in need thereof. In various embodiments, the method can comprise selecting the subject in need of treating short stature before administering the FGFR inhibitor to the subject.

In various embodiments, the short stature can be idiopathic short stature. In various embodiments, the subject does not have a germline FGFR mutation. In various embodiments, the subject can have an open growth plate. In various embodiments, the subject does not have cancer. In various embodiments, the subject does not have a brain tumor. In various embodiments, the subject can be a pediatric subject.

In various embodiments, the FGFR inhibitor can be a pan-FGFR inhibitor. In various embodiments, the FGFR inhibitor can be a selective-FGFR inhibitor. In various embodiments, the FGFR inhibitor can be ASP5878, AZD4547, debio 1347, TAS-120, HMPL-453, LY2874455, or pemigatinib. In various embodiments, the FGFR inhibitor can be erdafitinib.

In various embodiments, administering the FGFR inhibitor can comprise administering the FGFR inhibitor once a day orally. In various embodiments, administering the FGFR inhibitor can comprise administering the FGFR inhibitor multiple times a day orally. In various embodiments, the therapeutically effective amount of the FGFR inhibitor can be between 4.2-5.2 mg/m$^2$ per day. In various embodiments, the therapeutically effective amount of the FGFR inhibitor can be about 4.7 mg/m$^2$ per day. In various embodiments, the therapeutically effective amount of the FGFR inhibitor can be less than 4.7 mg/m$^2$ per day. In various embodiments, the therapeutically effective amount of the FGFR inhibitor can be less than 4.2 mg/m$^2$ per day. In various embodiments, the therapeutically effective amount of the FGFR inhibitor can be less than 3.7, 3.2, 2.7, 2.2, 1.7, 1.2, 0.7, or 0.2 mg/m$^2$ per day. In various embodiments, the therapeutically effective amount of the FGFR inhibitor can be less than 4.0, 3.5, 3.0, 2.5, 2.0, 1.5, 1.0 or 0.5 mg/m$^2$ per day.

In various embodiments, administering the FGFR inhibitor can comprise metronomic administration.

Various embodiments provide for a method of increasing a subject's height, comprising: administering a therapeutically effective amount of a FGFR inhibitor to the subject. In various embodiments, the method can further comprise selecting a subject in need of increasing his or her height before administering the FGFR inhibitor to the subject, or selecting a subject desiring to increase his or her height before administering the FGFR inhibitor to the subject.

In various embodiments, the subject can have an open growth plate.

In various embodiments, the subject does not have a germline FGFR mutation. In various embodiments, the subject does not have cancer. In various embodiments, the subject does not have a brain tumor. In various embodiments, the subject can be a pediatric subject.

In various embodiments, the FGFR inhibitor can be a pan-FGFR inhibitor. In various embodiments, the FGFR inhibitor can be a selective-FGFR inhibitor. In various embodiments, the FGFR inhibitor can be ASP5878, AZD4547, debio 1347, TAS-120, HMPL-453, LY2874455, or pemigatinib. In various embodiments, the FGFR inhibitor can be erdafitinib.

In various embodiments, administering the FGFR inhibitor can comprise administering the FGFR inhibitor once a day orally. In various embodiments, administering the FGFR inhibitor can comprise administering the FGFR inhibitor multiple times a day orally. In various embodiments, administering the FGFR inhibitor can comprise metronomic administration.

In various embodiments, the therapeutically effective amount of the FGFR inhibitor can be between 4.2-5.2 mg/m$^2$ per day. In various embodiments, the therapeutically effective amount of the FGFR inhibitor can be about 4.7 mg/m$^2$ per day. In various embodiments, the therapeutically effective amount of the FGFR inhibitor can be less than 4.7 mg/m$^2$ per day. In various embodiments, the therapeutically effective amount of the FGFR inhibitor can be less than 4.2 mg/m$^2$ per day. In various embodiments, the therapeutically effective amount of the FGFR inhibitor can be less than 3.7, 3.2, 2.7, 2.2, 1.7, 1.2, 0.7, or 0.2 mg/m$^2$ per day. In various embodiments, the therapeutically effective amount of the FGFR inhibitor can be less than 4.0, 3.5, 3.0, 2.5, 2.0, 1.5, 1.0 or 0.5 mg/m$^2$ per day.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
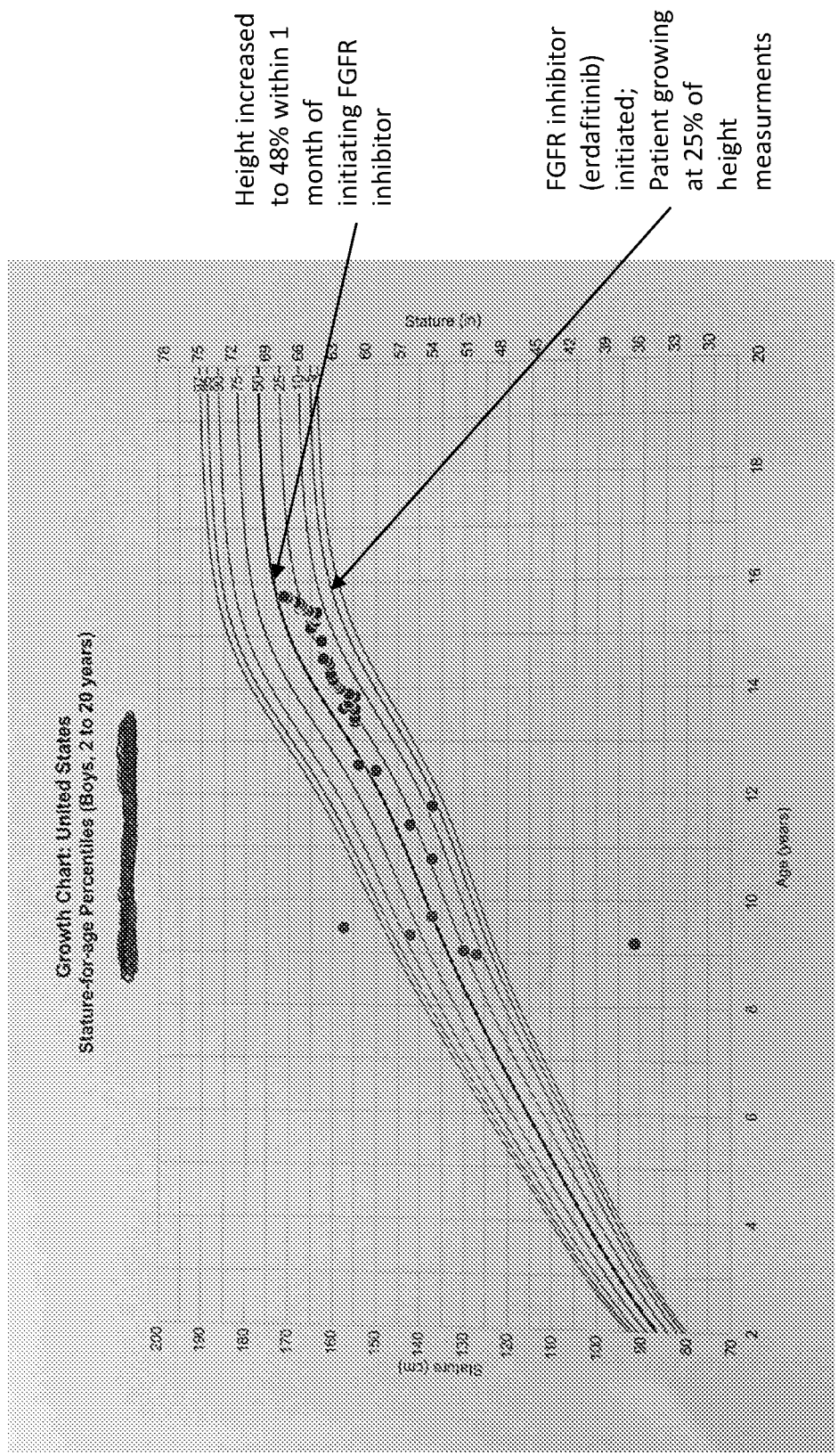
FIG. 1 depicts a 15-year old child's growth chart. His growth velocity accelerated beyond expected velocity thereby jumping from 15$^{th}$ percentile to 48$^{th}$ percentile within one month of initiating FGFR inhibitor treatment. His height increased from 15th percentile to 70$^{th}$ percentile in 10 months from the initiation of FGFR inhibitor treatment.
Figure 2:
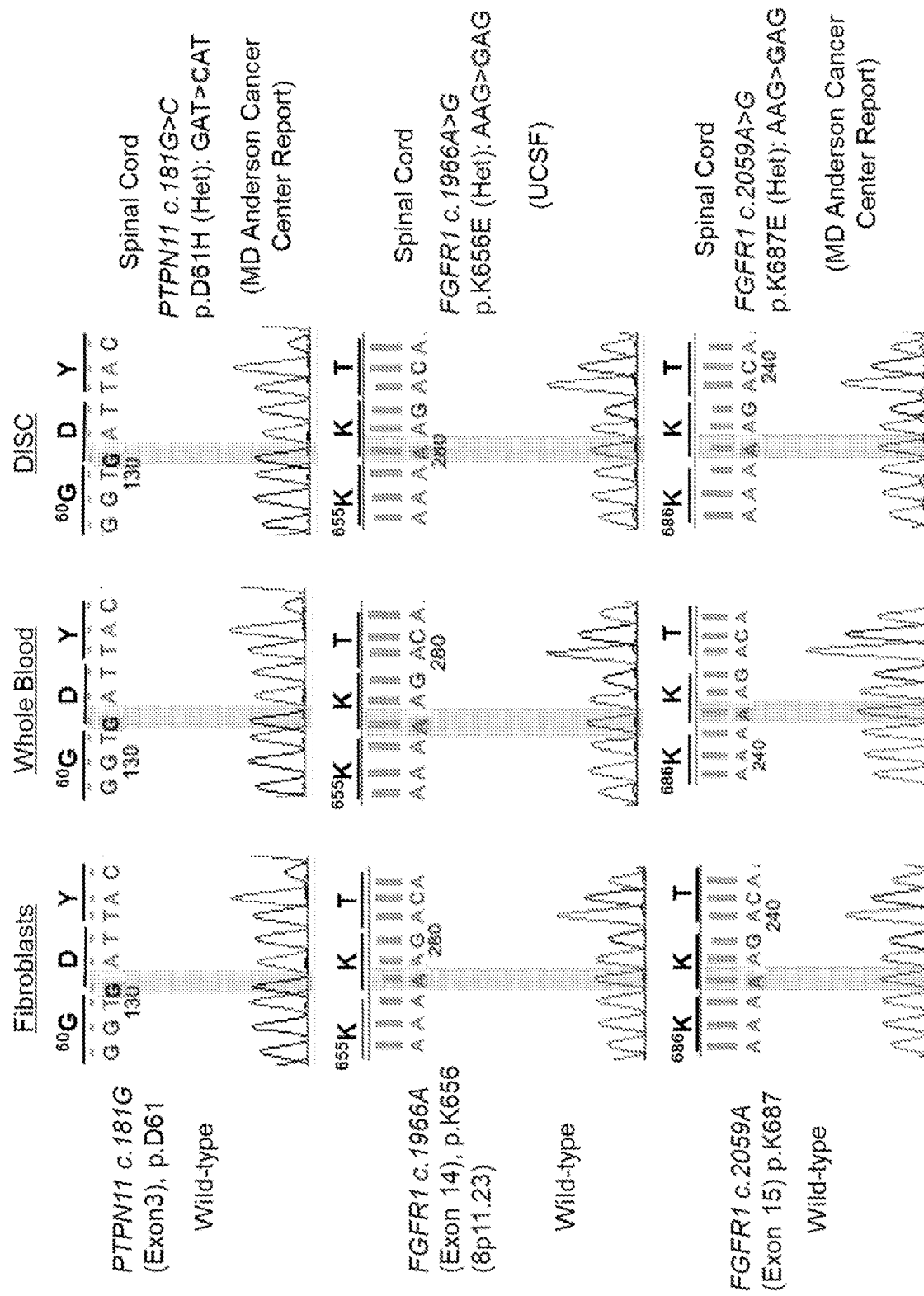
FIG. 2 depicts Sanger sequencing for patient CC0419. Sanger DNA sequencing confirmed that the PTPN11 and FGFR1 mutations identified in biopsy of the tumor, were normal in 3 different tissues/cells from same patient. Pathological PTPN11 and FGFR1 variants were not found in other tissues from the patient. This confirms that these mutations are tumor specific and not germline.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the term "about" when used in connection with a referenced numeric indication means the referenced numeric indication plus or minus up to 5% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 9%, 8%, 7%, 6%, 5%, 4%, 3%, 2%, or 1% of that referenced numeric indication, if specifically provided for in the claims.

"Therapeutically effective amount" as used herein refers to that amount which is capable of achieving beneficial results in a patient with idiopathic short stature, or a patient in need of increasing his or her height, or a patient who desires an increase in his or her height. A therapeutically effective amount can be determined on an individual basis and will be based, at least in part, on consideration of the physiological characteristics of the mammal, the type of delivery system or therapeutic technique used and the time of administration relative to the progression of the disease or disorder.

"Beneficial results" include, but are in no way limited to, lessening or alleviating the severity of the disease or disorder or its complications, preventing or inhibiting it from manifesting, preventing or inhibiting it from recurring, merely preventing or inhibiting it from worsening, curing the disease or disorder, reversing the progression of the disease or disorder, prolonging a patient's life or life expectancy, ameliorating the disease or disorder, or a therapeutic effort to effect any of the aforementioned, even if such therapeutic effort is ultimately unsuccessful.

A "healthy subject" or "normal subject" is a subject (e.g., patient) who does not have the disease or disorder that is being treated in the subject in need thereof.

"Treatment" and "treating," as used herein refer to both therapeutic treatment and prophylactic or preventative measures, wherein the object is to prevent, slow down and/or lessen the disease or disorder even if the treatment is ultimately unsuccessful.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. In some embodiments, the subject is a human. In some embodiments, the subject is a pediatric subject.

Various embodiments of the present invention provide for a method for treating short stature, comprising: administering a therapeutically effective amount of a FGFR inhibitor to a subject in need thereof. In various embodiments, the method comprises selecting a subject in need of treatment for short stature before administering the FGFR inhibitor. Selecting the subject need of treatment for short stature is or can be based on the recognition that an FGFR inhibitor would provide beneficial effects to the subject, including but not limited to increasing the subject's height.

Various embodiments of the present invention provide for a method of increasing a subject's height, comprising: administering a therapeutically effective amount of a FGFR inhibitor to a subject in need thereof. In various embodiments, the method comprises selecting a subject in need of treatment for to increase the subject's height before administering the FGFR inhibitor. Selecting the subject need of treatment for increasing his or her height is or can be based on the recognition that an FGFR inhibitor can increase the subject's height in absence of a FGFR mutation.

In various embodiments, the short stature is idiopathic short stature. In various embodiment, the subject with idiopathic short stature has normal growth hormones. In various embodiments, the subject does not have a germline FGFR mutation.

In various embodiments, the subject does not have cancer. In various embodiments, the subject does not have a brain tumor. In various embodiments, the subject has cancer but a cancer other than a brain tumor or brain cancer.

In various embodiments, the subject is a patient with open growth plate. In various embodiments, the subject is 1 month to 2 years. In various embodiments, the subject is over 2 years (e.g., 2 years and one day) to 12 years. In various embodiments, the subject is over 12 years (e.g., 12 years and one day) to 16 years. In various embodiments, the subject has not reached his or her adult height. In various embodiments, the subject is over 16 years (e.g., 16 years and one day) to 18 years.

In various embodiments, the FGFR inhibitor is a pan-FGFR inhibitor. In various embodiments, the FGFR inhibitor is a selective-FGFR inhibitor; for example, selective for FGFR1, FGFR2, FGFR3, or FGFR4. In various embodiments, the FGFR inhibitor is ASP5878, AZD4547, debio 1347, TAS-120, HMPL-453, LY2874455, or pemigatinib. In particular embodiments, the FGFR inhibitor is erdafitinib.

In various embodiments, administering the FGFR inhibitor comprises administering the FGFR inhibitor once a day; for example, orally. In various embodiments, administering the FGFR inhibitor comprises administering the FGFR inhibitor multiple times a day. In various embodiments, administering the FGFR inhibitor comprises administering the FGFR inhibitor 2, 3, 4, or 5 times a day. In various embodiments, administering the FGFR inhibitor comprises administering the FGFR inhibitor 2 or 3 times a day.

In various embodiments, FGFR inhibitor comprises administering the FGFR inhibitor once a week, two times a week, or three times a week.

In various embodiments there is metronomic administration of the FGFR inhibitor with periods of rest or drug holidays. That is, there are periodic amounts of times where the child is not receiving the FGFR inhibitor (e.g., erdafitinib). Examples of drug holidays include but are not limited to one day per a week, two days per week, one day every 2 weeks, one week per month, one week per 3 months, one week per 6 months, one week per 9 months, one week per 12 months, one month per 3 months, one month per 6 months, one per 9 months, or one month per year, or combinations thereof. In various embodiments, metronomic administration of the FGFR inhibitor also comprises administering a low amount of the FGFR inhibitor. For example, if a therapeutically effective amount of the FGFR inhibitor is between 4.2-5.2 mg/m$^2$ per day, that amount can be reduced by administering ½, ⅓, ¼, ⅕, ⅙, 1/10, 1/15, 1/20, 1/25, 1/50, or 1/100 of the 4.2-5.2 mg/m$^2$ per day. Metronomic administration usually comprises administering over a longer overall period of time. For example, 1.0, 1.3, 2.0, 2.4, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5 or 16.0 years.

In various embodiments, administering the FGFR inhibitor comprises administering the FGFR inhibitor for about 1-3 months. In various embodiments, administering the FGFR inhibitor comprises administering the FGFR inhibitor for about 4-6 months. In various embodiments, administering the FGFR inhibitor comprises administering the FGFR inhibitor for about 7-9 months. In various embodiments, administering the FGFR inhibitor comprises administering the FGFR inhibitor for about 9-12 months. In various embodiments, administering the FGFR inhibitor comprises administering the FGFR inhibitor for about 1 year. In various embodiments, administering the FGFR inhibitor comprises administering the FGFR inhibitor for about 18 months. In various embodiments, administering the FGFR inhibitor comprises administering the FGFR inhibitor for about 2 years. In various embodiments, administering the FGFR inhibitor comprises administering the FGFR inhibitor for about 2.5 years. In various embodiments, administering the FGFR inhibitor comprises administering the FGFR inhibitor for about 3 years. In various embodiments, administering the FGFR inhibitor comprises administering the FGFR inhibitor for about 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5 or 16.0 years. In various embodiments, administering the FGFR inhibitor comprises administering the FGFR inhibitor until the subject reaches his or her adult height.

In various embodiments, the therapeutically effective amount of the FGFR inhibitor is between 4.2-5.2 mg/m$^2$ per day. In various embodiments, the therapeutically effective amount of the FGFR inhibitor is about 4.7 mg/m$^2$ per day. In various embodiments, the therapeutically effective amount of the FGFR inhibitor is less than 4.7 mg/m$^2$ per day. The therapeutically effective amount can be divided into multiple doses per day; for example, 2, 3, 4 or 5 doses per day.

In various embodiments, the therapeutically effective amount of the FGFR inhibitor is less than 4.2 mg/m$^2$ per day. In various embodiments, the therapeutically effective amount of the FGFR inhibitor is less than 3.7, 3.2, 2.7, 2.2, 1.7, 1.2, 0.7, or 0.2 mg/m$^2$ per day. In various embodiments, the therapeutically effective amount of the FGFR inhibitor is less than 4.0, 3.5, 3.0, 2.5, 2.0, 1.5, 1.0 or 0.5 mg/m$^2$ per day. The therapeutically effective amount can be divided into multiple doses per day; for example, 2, 3, 4 or 5 doses per day.

In various embodiments, the effective amount of the FGFR inhibitor is any one or more of about 0.001-0.01, 0.01-0.1, 0.1-0.5, 0.5-1, 1-2, 2-3, 3-4, 4-5, 5-6, 6-7, 7-8, 8-9, or 9-10 mg/m$^2$/day, or a combination thereof.

In various embodiments, the effective amount of the FGFR inhibitor is any one or more of about 0.001-0.01, 0.01-0.1, 0.1-0.5, 0.5-1, 1-2, 2-3, 3-4, 4-5, 5-6, 6-7, 7-8, 8-9, or 9-10, µg/m$^2$/day, or a combination thereof.

In various embodiments, the effective amount of the FGFR inhibitor can be reduced during the administration period.

Here, "mg/m$^2$/day" refers to mg agent per m$^2$ body surface area of the subject per day; and "µg/m$^2$/day" refers to µg agent per m$^2$ body surface area of the subject per day.

In various embodiments, the present invention the FGFR inhibitor is provided as a pharmaceutically acceptable salt or prodrug.

In various embodiments the FGFR inhibitor is altered for tissue selectivity to concentrate it in the bone or the growth plate. In various embodiments the FGFR inhibitor is a prodrug that is converted to its active form in bone or only at the growth plate. In various embodiment the FGFR inhibitor is altered so that it cannot cross the blood-brain barrier. In various embodiments, the FGFR inhibitor is attached to an antibody that concentrates it in specific tissue including but not limited to chondrocytes or the growth plate. For example, the FGFR inhibitor is attached to an antibody (or a fragment thereof) capable of binding to chondrocytes, or an antibody (or a fragment thereof) capable of binding to the growth plate.

In various embodiments, the present invention provides pharmaceutical compositions including a pharmaceutically acceptable excipient along with a therapeutically effective amount of the FGFR inhibitor. "Pharmaceutically acceptable excipient" means an excipient that is useful in preparing a pharmaceutical composition that is generally safe, nontoxic, and desirable, and includes excipients that are acceptable for veterinary use as well as for human pharmaceutical use. Such excipients may be solid, liquid, semisolid, or, in the case of an aerosol composition, gaseous.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals such as sodium, lithium, potassium, calcium, magnesium and the like, as well as nontoxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "pharmaceutically acceptable esters" refers to the relatively nontoxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active one or more peptides as disclosed herein or a mutant, variant, analog or derivative thereof. A thorough discussion is provided in T. Higachi and V. Stella, "Pro-drugs as Novel Delivery Systems," Vol. 14 of the A. C. S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. A prodrug of the one or more peptides as disclosed herein or a mutant, variant, analog or derivative thereof can be designed to alter the metabolic stability or the transport characteristics of one or more peptides as disclosed herein or a mutant, variant, analog or derivative thereof, to mask side effects or toxicity, to improve the flavor of a compound or to alter other characteristics or properties of a compound. By virtue of knowledge of pharmacodynamic processes and drug metabolism in vivo, once a pharmaceutically active form of the one or more peptides as disclosed herein or a mutant, variant, analog or derivative thereof, those of skill in the pharmaceutical art generally can design prodrugs of the compound (see, e.g., Nogrady (1985) Medicinal Chemistry A Biochemical Approach, Oxford University Press, N. Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The*

*Science and Practice of Pharmacy* (Gennaro ed. 20th edition, Williams & Wilkins PA, USA) (2000).

Kits

The present invention is also directed to a kit to treat short stature. The kit is useful for practicing the inventive method of treating short stature. The kit is an assemblage of materials or components, including at least one of the inventive compositions. Thus, in some embodiments the kit contains a composition including an FGFR inhibitor, pharmaceutically acceptable salt there of or pharmaceutically acceptable prodrug thereof as described above.

The exact nature of the components configured in the inventive kit depends on its intended purpose. For example, some embodiments are configured for the purpose of treating short stature. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treating short stature. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a FGFR inhibitor. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Missense mutations in Fibroblast growth factor receptor (FGFR) signaling plays essential roles in bone development and disease. Missense mutations in humans can cause various congenital bone diseases, including skeletal dysplasia and craniosynostosis, resulting in skull deformity or short stature.

A 15-year old child with diffuse intracranial pilocytic astrocytoma with somatic tumor FGFR1 mutation was started on the FGFR inhibitor Erdafitinib. The child was found to have wildtype germline FGFR.

In the absence of an activating systemic FGFR mutation, Erdafitinib therapy resulted in dramatic jump in growth velocity from 40% to >99% (3.653 cm/year to 18.06 cm/year).

CC0419-P1 Diagnosis: Male, age 15 yrs (early puberty), with pilocytic astrocytoma, in C1 meninges.

Pathological variants identified in tumor tissue, both activating:
  PTPN11 (Protein Tyrosine Phosphatase Non-Receptor Type 11) p.D61H (het, exon 3)
  FGFR1 (Fibroblast Growth Factor Receptor 1) p.K656E (het, exon 14) or p.K687E (het, exon 15) (from different reports)

Treatment started when Tanner 3-4:

Treated with erdafitinib: tumor responded to therapy with significant reduction in tumor burden. Height went from ~15 percentile to 23 percentile, starting ~ 2 months into therapy.

Clinical indication: unusual rapid growth on erdafitinib. Musculoskeletal problems including rapid growth and kyphosis/scoliosis which required surgery. Transient hyperphosphatemia normalized after coming off erdafitinib. Post-erdafitinib, pre-operative, DEXA axial bone scan consistent with osteoporosis (bone density −3.8 SD)

no DEXA performed pre-erdafitinib treatment.

Post-erdafitinib treatment, x-ray hand and wrist:
  bone age delayed ~2 yrs compared to CA (16.2 yrs).
  Periosteal reaction (distal radius, ulna, first metacarpal)—may be secondary to hyperphosphatemia as side effect of drug
  A suggestion of osteochondrosis (slight cortical irregularity of articular surface of second metacarpal head)

Post-erdafitinib (@16.2 yrs):
  Testosterone, free and total-abnormally low (for Tanner 3-5; not sure of Tanner stage post-treatment).
  GH, random: normal
  IGF-II: normal
  IGF-I: low-normal (256 ng/ml, normal range 209-602 ng/ml; −1.4 SDS)
  IGFBP-3: normal
  Metabolic panel: creatine-below normal; alkaline phosphatase, ALP—high (746 U/L, NR 89-365 U/L)
  CBC panel: RDW (red cell distribution width) above normal (16.4%, NR 11.6-14.4%)

This is the case of a 17-year-old male with an initial diagnosis at the age of 9 years of pilomyxoid astrocytoma of the sacral (S1) region with leptomeningeal dissemination. He received chemotherapy comprised of carboplatin and vincristine courses over a period of 65 weeks until the age of 11-years and six-months and upon recurrence courses of vinblastine, irinotecan, and bevacizumab from the age of 13-years and seven-months to 14-years and six-months.

At the age of 14-years and ten-months, he underwent a biopsy for a second recurrence. The Next-generation gene sequencing of the tumor conducted at Cedars-Sinai Medical Center (CSMC) in Los Angeles and the University of California San Francisco (UCSF) identified activating PTPN11 and activating FGFR1 mutations. At that time, a diagnosis of "Rosette-forming glioneuronal tumor with anaplastic features" was favored. Upon progression of the tumor following two cycles of procarbazine, lomustine, and vincristine, he was enrolled on the Pediatric MATCH (Molecular Analysis for Therapy Choice) screening Study APEC1621SC (NCT03155620), and the tumor tissue previously obtained was sent to the study-approved Laboratory which confirmed the presence of actionable target FGFR1 gene mutation and the availability of an FGFR inhibitor, Erdafitinib (JNJ-42756493). The consent for the study APEC1621B (NCT03210714) was obtained from the patient and his father, and the patient started treatment with Erdafitinib (JNJ-42756493) at the age of 15-years and four-months at an initial dose of 7 mg orally daily for 5 months followed by a reduced dose of 5 mg daily during the last 4 months of therapy. The dose was changed due to adverse events including, musculoskeletal pain and high phosphorus levels requiring administration of high doses of oral phosphorus binders and frequent interruptions of therapy.

It was noted that during the 9-month period of Erdafitinib (JNJ-42756493) therapy and for one month after cessation of the treatment, he grew a total of 14.3 cm (5.63 inches), jumping from growth along the approximately 15.8th percentile to 69.8th percentile of his growth curve. The drug was ultimately discontinued due to the development of scoliosis of the thoracic region, kyphosis of the upper cervical region, and hip flexion contractures, all of which were considered related to the rapid skeletal growth that was not reciprocated by musculature and the other soft tissues growth. It is important to note that his height could not be accurately measured during the last few months due to his inability to stand straight.

About one month following the cessation of Erdafitinib (JNJ-42756493), a bone age, bone density, and biochemistry laboratory work-up were performed. Bone age showed delayed chronological age, most similar to a 14-year old, which is greater than 2 standard deviation below the mean.

On the Bone density/Dexa bone scan, the mean bone density value for the lumbar spine measured 0.6322 gm/sq·cm, which is 3.8 standard deviations below the mean value for age-matched population and more than 2.5 standard deviations below the value for males at peak bone mass. These findings were consistent with osteoporosis. However, since DEXA scans were not performed prior to Erdafitinib (JNJ-42756493) therapy, it was unclear if the osteoporotic symptoms were independent of Erdafitinib (JNJ-42756493) therapy or therapy contributed to it.

Biochemistry work-up following the cessation of Erdafitinib (JNJ-42756493) are as follows:

| Tests | Patient's Values | Normal Values |
|---|---|---|
| Testosterone Free | 1.1 pg/mL | 18-111.0 pg/mL |
| Testosterone Total | 13 ng/dL | Male prepubertal stage I <5 ng/dL male pubertal stage II <67 ng/dL male pubertal stage III: 21-719 ng/dL male pubertal stage IV: 25-912 ng/dL Male pubertal stage V: 110-975 ng/dL |
| Growth Hormone | 2.7 ng/mL | <10.1 ng/mL |
| IGF-2 | 621 ng/dL | Prepubertal: 258-882 ng/mL Pubertal: 273-872 ng/mL |
| IGF-1 | 256 ng/mL | |
| Z-score | −1.7 | |
| IGF binding protein-3 | 5.8 mg/dL | 3.4-9.5 mg/dL |

-continued

| Tests | Patient's Values | Normal Values |
|---|---|---|
| (IGFBP-3) Glucose | 84 mg/dL | 70-99 mg/dL |
| Electrolytes | | |
| Magnesium | 1.9 mg/dL | 1.7-2.2 mg/dL |
| Phosphorus | 3.7 mg/dL | 2.3-4.7 mg/dL |
| Calcium | 9.6 mg/dL | 8.4-10.2 mg/dL |
| Potassium | 3.8 mmol/L | 3.5-5.0 mmol/L |
| Sodium | 135 mmol/L | 135-145 mmol/L |
| Kidney Function | | |
| BUN | 17 mg/dL | 8.4-21 mg/dL |
| Creatinine | 0.4 mg/dL | 0.65-1.04 mg/dL |
| Liver Function | | |
| Total bilirubin | 0.3 mg/dL | 0.3-1.2 mg/dL |
| Alkaline phosphatase | 746 U/L | 89-365 U/L |
| ALT | 22 U/L | 0-55 U/L |
| AST | 27 U/L | 5-34 U/L |

Example 2

Material & Methods

All reagents are commercially available, including erdafitinib, FDA-approved small molecular inhibitor known to block signaling from all 4 FGF receptors, FGFR1-4. We use FGF2 to activate FGFR. Primary bone marrow human mesenchymal cells (hMSC) were purchased from Lonza. All methods are standard, routinely used for analyzing signaling, cell survival and growth.

Results

Figure 3:
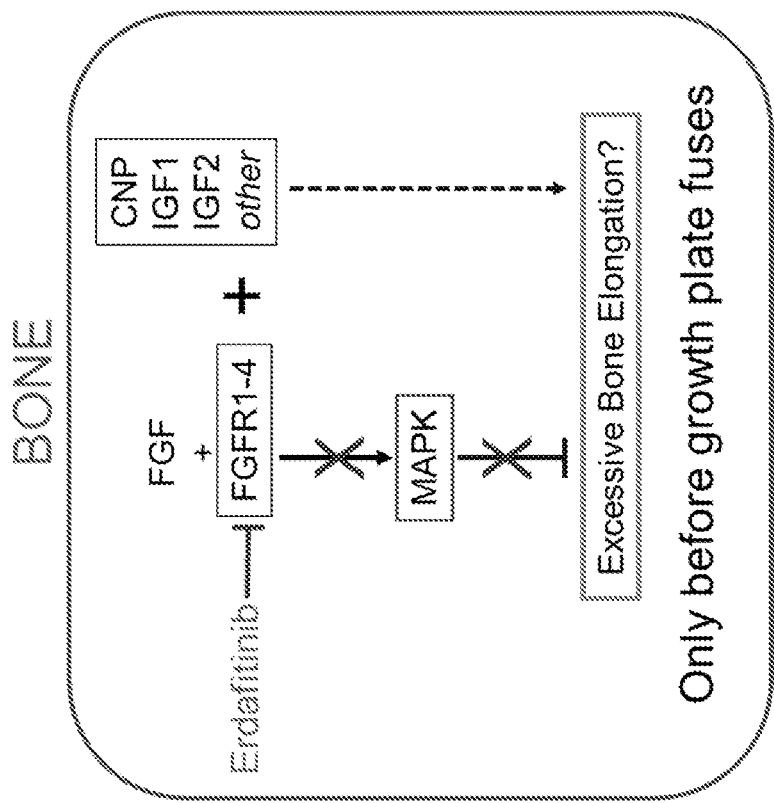
FIG. 3 shows a mechanism for achondroplasia: bone elongation inhibited by activating FGFR3, inactivating NPR2 or CNP, mutations; and a possible mechanism for the effects of erdafitinib action on bone growth. This patient is not a achondroplastic dwarf, and did not have a germline mutation in the FGFR pathways. Therefore, his growth from the drug cannot be explained to be a result of blocking an activating mutation that is present in Achondroplastic dwarfism and is reversed by using a pan-FGFR inhibitor.
Figure 3:
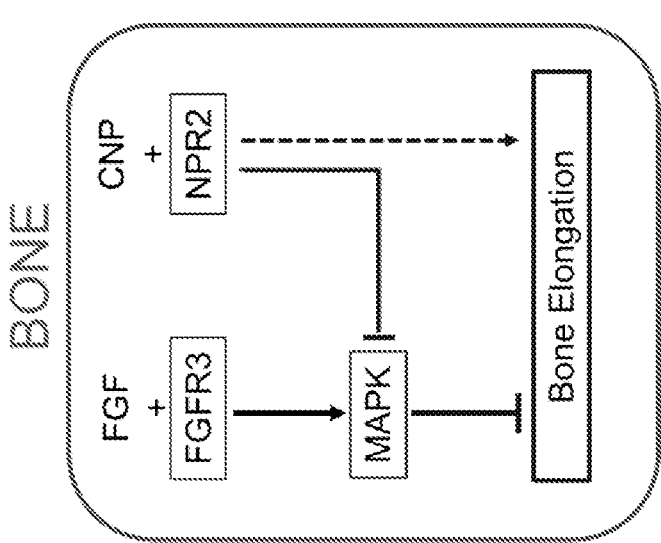
Figure 4:
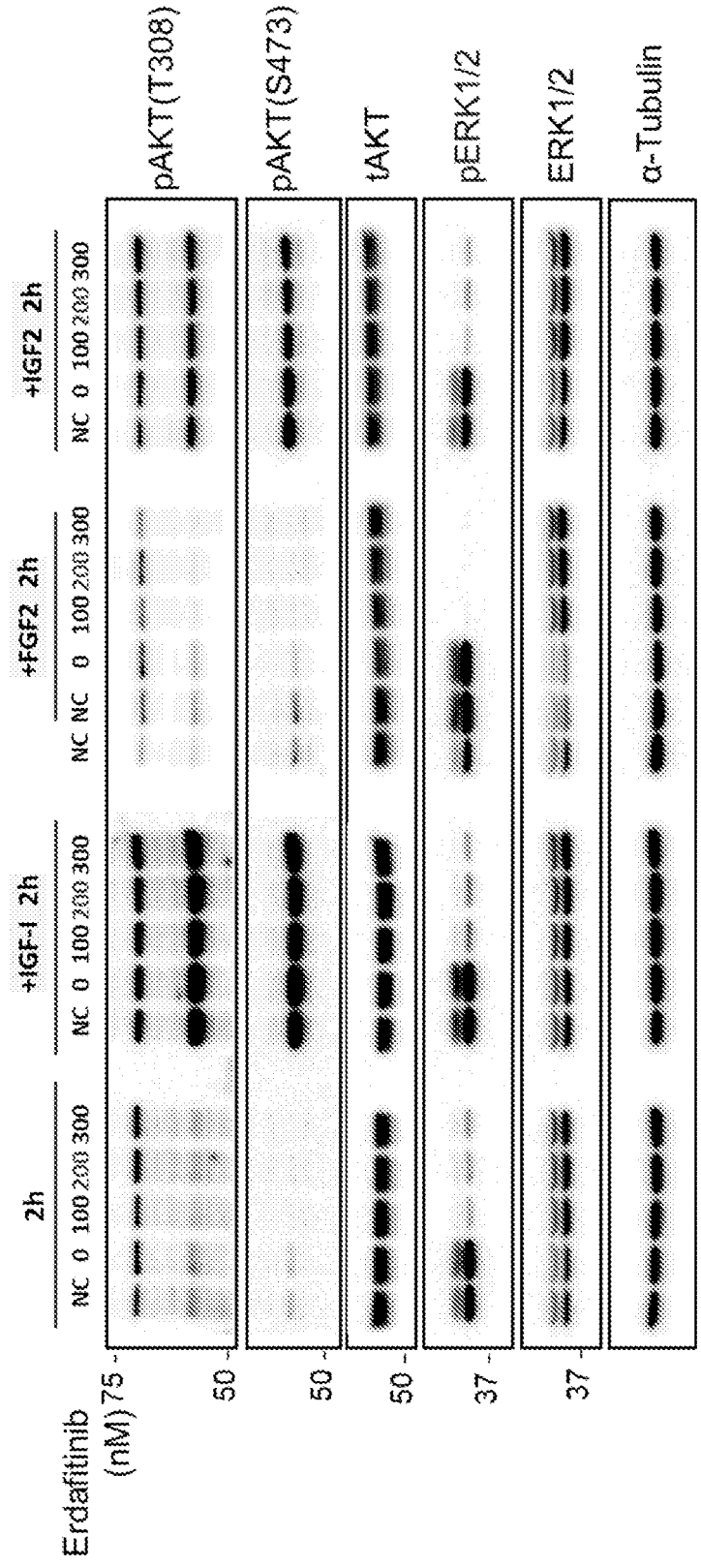
FIG. 4 depicts signaling effects. Patient normal fibroblast cells: signaling inhibition by Erdafitinib can be partially reversed by IGF-I and IGF2 but not by FGF2. Test working hypothesis using Patient's normal fibroblast cells as the model system. Fibroblasts, grown in αMEM+15% FBS till ~80% confluency, were serum-starve for 18 hr in αMEM+ 0.1% BSA. Cells were then pre-treated with erdafitinib (0-300 nM) for 30 min, prior to addition of indicated growth factors (IGF-I, 100 ng/ml; FGF2, 40 ng/ml; IGF-2, 100 ng/ml). Cell lysates, collected 2 hr post-treatment, were immunoblot analyzed for AKT and ERK1/2 signaling:
  Erdafitinib at 100 nM-300 nM: strongly suppressed background activated pERK1/2 and pAKT signaling (NC and "0", no erdafitinib controls). ERK1/2 is one of MAPK pathways.
  pERK1/2 remains erdafitinib-suppressed even in presence of ligands (IGF-1, IGF2).
  IGF-I and IGF-2 activates pAKT (NC, 0), and remains activated in presence of all concentrations of erdafitinib.
Figure 5:
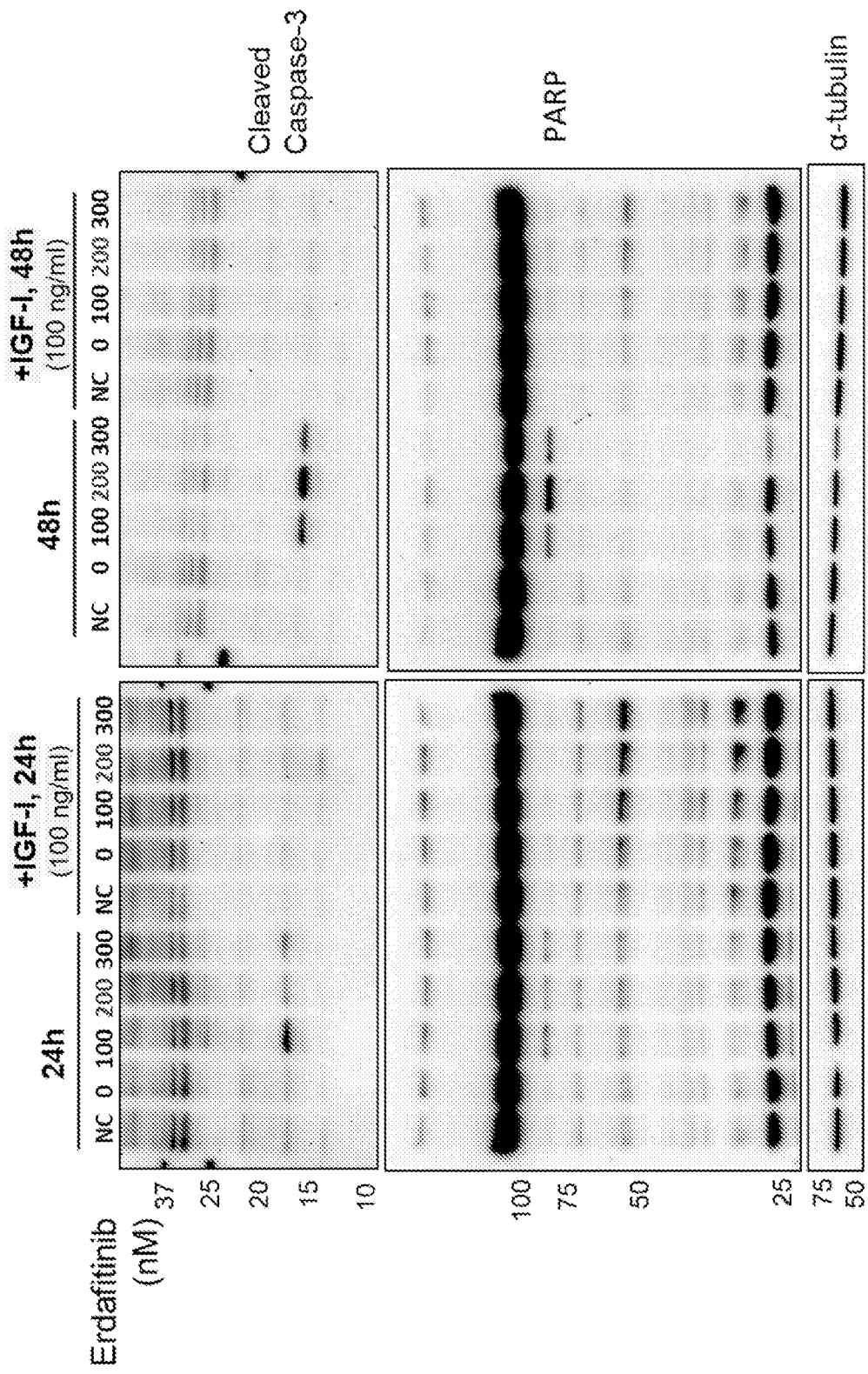
FIG. 5 depicts the effects on apoptosis. Patient normal fibroblasts: Erdafitinib-induced apoptosis can be reversed by IGF-I. Cells were grown and treated as in FIG. 4, except cell lysates were collected 24 and 48 hr post-treatment and analyzed by immunoblot analysis for apoptosis markers (i.e. cell death markers):
  By 24 hrs, apoptotic markers, cleaved Caspase 3 and cleaved PARP, are detected in erdafitinib treated cells.
  Apoptotic markers were not detected (or significantly blunted) when IGF-I was present. Therefore, IGF-I induction of AKT is prevent apoptosis in erdafitinib treated cells.
Figure 6:
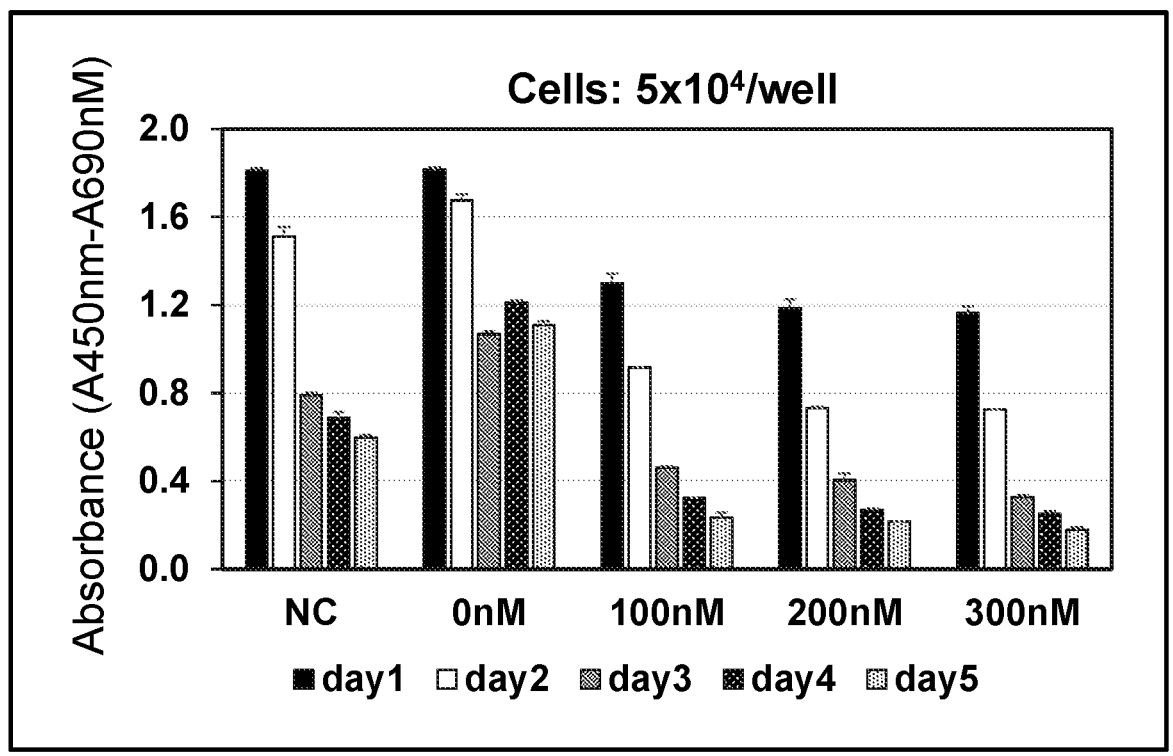
FIG. 6 depicts Cell Survival Assay (WST-1) for erdafitinib treatment, dose and time. Erdafitinib Decreases Cell Survival. Fibroblasts were seeded 5×10$^4$ cells/well (96 well format), grow in αMEM+15% for 24 hr. Serum-starve for 18 hr in αMEM+0.1% BSA and treated with erdafitinib (0-300 nM) for 1-5 days. WST-1 reagent was added, 10 μl/well, 1 hr, spectrophotometry analysis. 3 wells per test sample. NC, normal control. 5×10$^4$ cells/well appears to be the best cell density for performing assay. Patient normal fibroblast cells-erdafitinib decreases cell survival. Cell Survival Assay (using WST-I kit from Roche, catalogue 1644807) Interpretation: Range of cells/well were tested (not shown) and 5×10$^4$ cell/well was optimal. Serum-free media not conducive for cell proliferation but sufficient for monitoring cell survival. Erdafitinib dose-dependently decreased survival in serum-free media.
Figure 7:
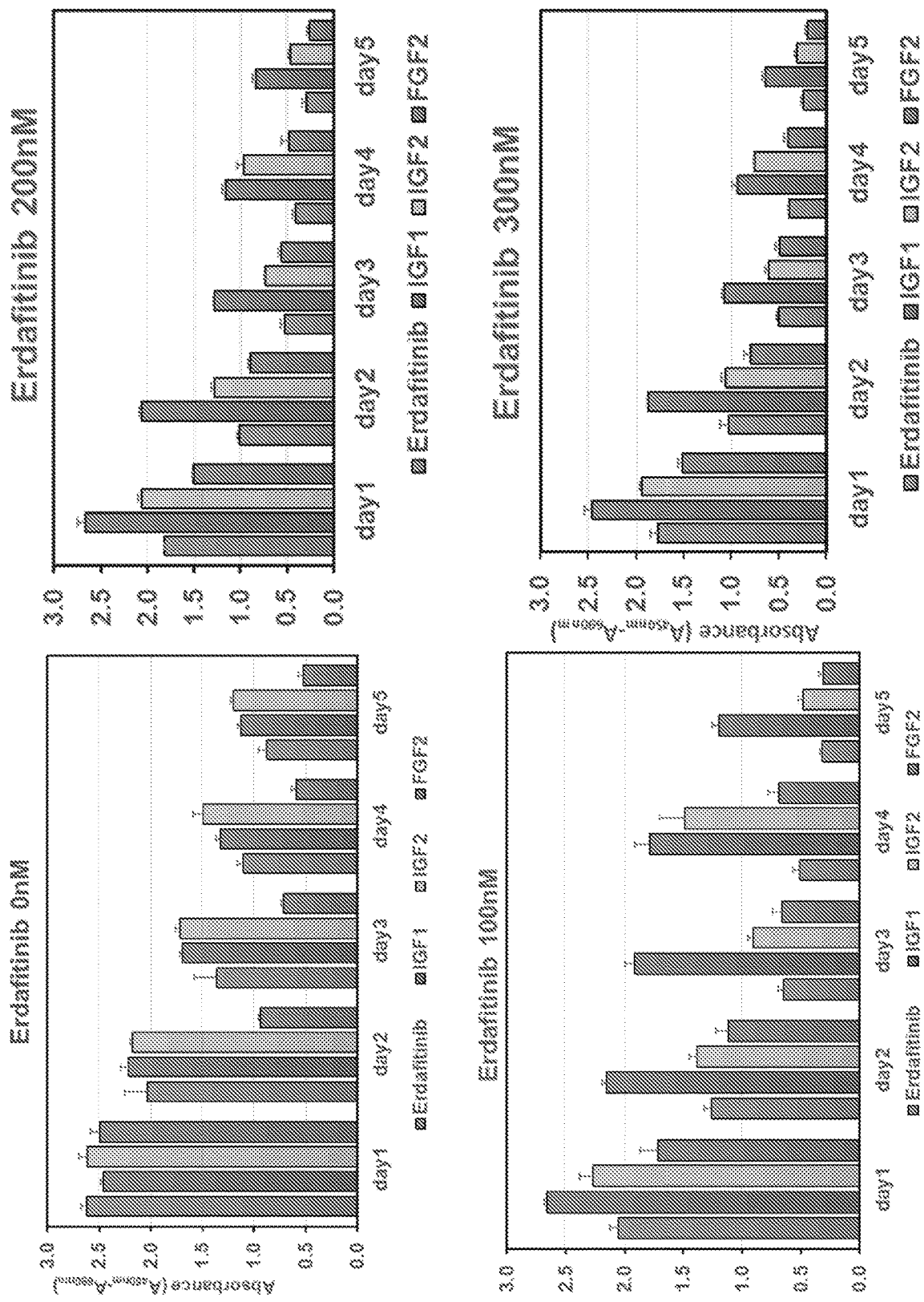
FIG. 7 depicts WST-I Assay—erdafitinib with and without growth factors. Patient normal fibroblast cells—test if growth factors can improve survival of erdafitinib-treated cell (WST-I assay). Assay set up as described in FIG. 6, except IGF-I (100 ng/ml), IGF2 (100 ng/ml) or FGF2 (40 ng/ml) added as indicated. Cell survival was assayed over 5 days. Note: "erdafitinib" bar means erdafitinib only, no growth factor added. Erdafitinib dose-dependently decreased survival in serum-free media (blue bars) as was shown in FIG. 6. IGF-I, but not FGF2, has significant protective effects on survival of cells.
Figure 8A:
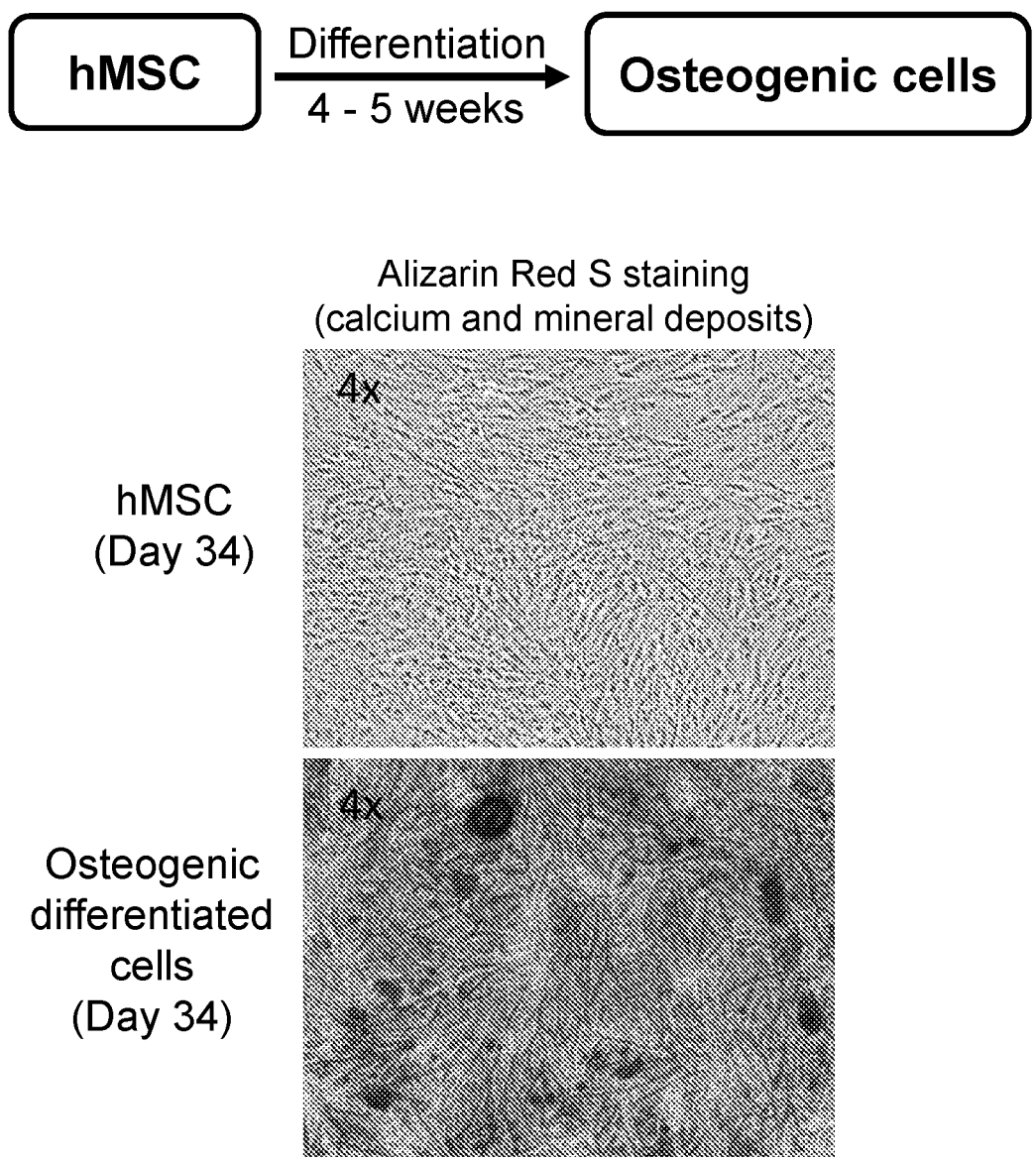
FIGS. 8A and 8B shows that effects of erdafitinib and IGF-I very similar to that seen with Patient's fibroblast cells. Primary Human Mesenchymal Stem Cells (hMSC) Differentiated to Osteogenic cells: AKT signaling inhibition by Erdafitinib is reversed by IGF-I. Osteogenic cells derived from hMSC-Data indicate effects of erdafitinib and IGF-I very similar to that seen with Patient's fibroblast cells. hMSC were seeded at 3×10$^4$ cells/well (6 well plate, collagen I coated). One set maintained in normal media, the other set, in osteogenic differentiating media. After indicated 4-5 weeks of differentiation, cells were stained with alizarin red S staining, which stains calcium and mineral deposits. Positive staining was seen only in osteogenic-like cells, not in hMSC. After differentiation period, osteogenic cells were placed in serum free media from 18 hr, pretreated with erdafitinib for 30 min (0, or 200 nM) prior to treatment with IGF-I, 100 ng/ml, for 0.5 h. We did not have enough wells of hMSC to treat with IGF-I. Cell lysates were collected and immunoblot analyzed as for primary patient fibroblasts. Interpretation of results: very similar to results of primary fibroblasts.
Figure 8B:
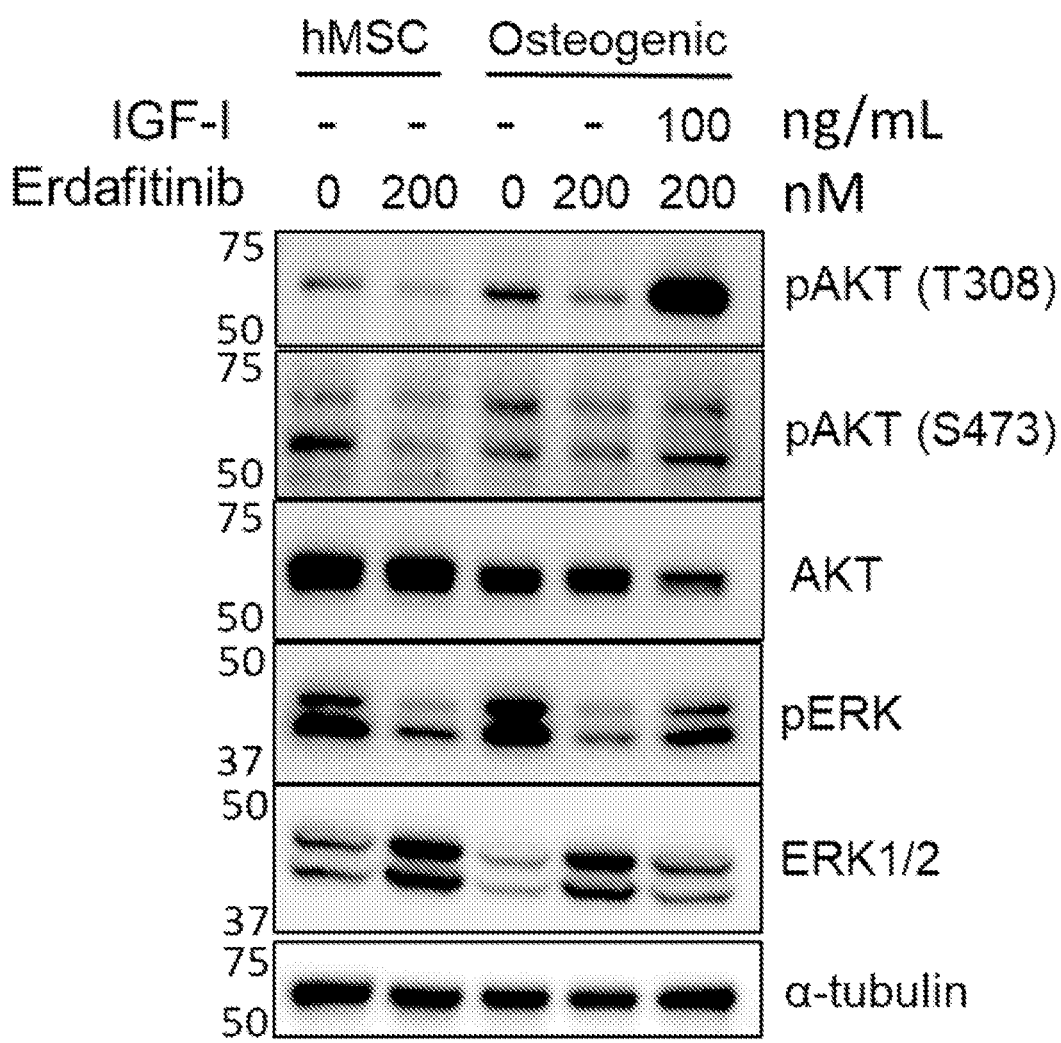
Figure 9:
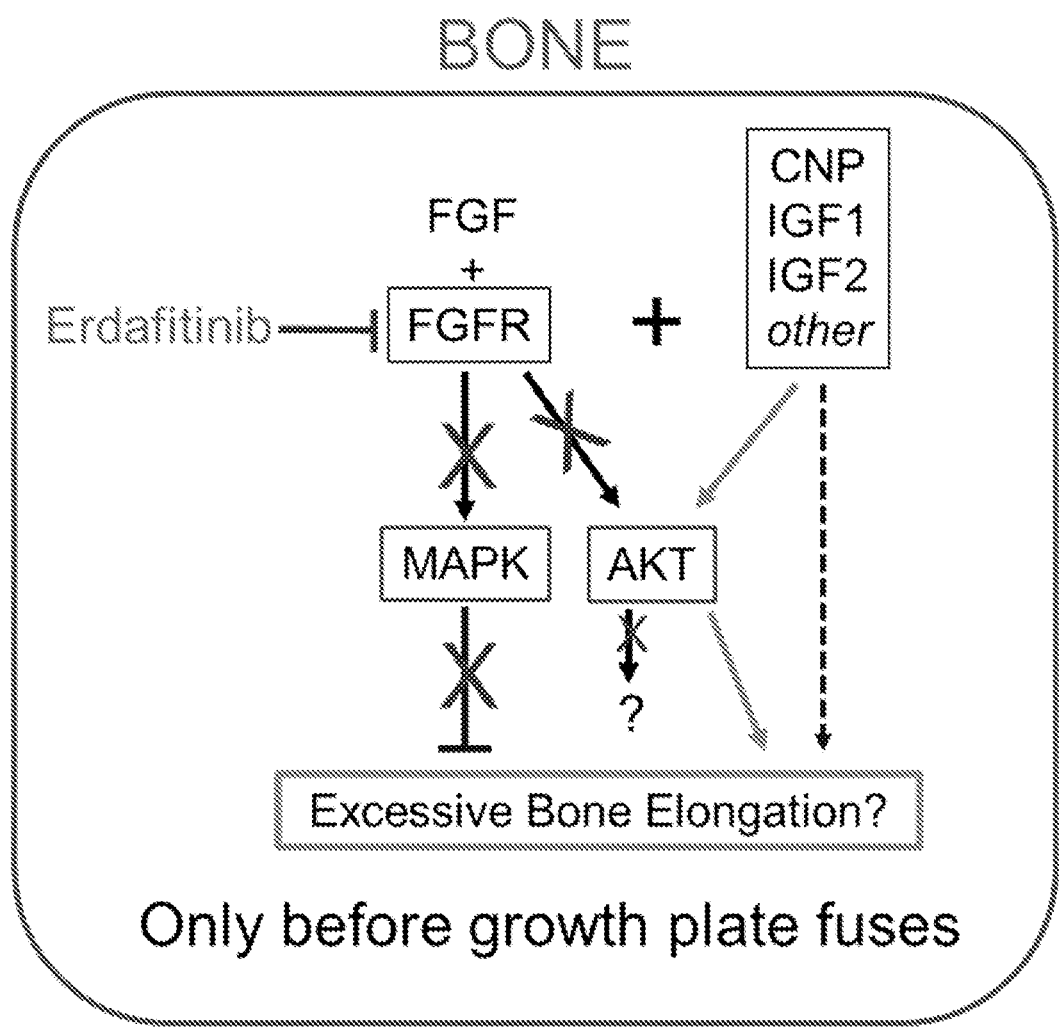
FIG. 9 depicts an updated possible mechanism: activation of FGFR signaling has negative effects on bone growth which, when FGFR is blocked by erdafitinib acts synergistically with positive growth/survival effects of IGF-I (and other growth factors and hormones), and lead to excessive bone elongation but before growth plate fuses (e.g., in growing children). Activation of AKT signaling independent of erdafitinib effects contributes to excessive bone elongation.

Normal bone growth involves a combination of negative and positive effectors. FGFR1 signaling has a negative effect on bone growth, evidenced by clinical condition of achondroplasia (severe short-limbed dwarfism) caused by activating FGFR mutations which leads to activated MAPK signaling and subsequent inhibition of bone elongation. CNP and NPR2 are positive effectors that can counter activated FGFR. However, inactivating mutations in CNP and NPR2 cannot counter activated FGFR and, therefore, also lead to achondroplasia. (FIG. 3.)

In normal bone (of patient), while not wishing to be bound by any particular theory, we believe that Erdafitinib blocks negative effects of FGFR signaling, which, together with positive effects other growth factors and hormones, acts synergistically (essentially positive+positive effectors) and result in excessive bone elongation but only before growth plate fuses (i.e. in growing children). (FIG. 3.)

We assess effects of erdafitinib on growth/survival of normal cells, in presence of growth factors such as IGF-I and IGF-2, comparing to FGF2. In vitro assays, with read-outs: signaling (pERK, pAKT), proliferation/survival assays (WST-1). Cell types:

Patient fibroblasts: although not ideal cell type, we can obtain some information about effects of erdafitinib.

hMSC: primary, normal, human mesenchymal cells (purchased), compare to hMSC differentiated into osteogenic cells-see effects of inhibitor+/−growth factors.

Additional results are depicted and discussed in FIGS. 4-9.

Example 3

A 10-year-old child presents with short stature. A therapeutically effective amount of erdafitinib is administered to the child over a six-month period. His height growth velocity increased resulting in a jump in height from the 10% up to the 50% for his age.

An 8-year-old child with open growth plates presents with idiopathic short stature. An effective amount of erdafitinib is metronomic administered to the child over an 8-year period, wherein there are drug holidays of one week out of each month.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Groupings of alternative elements or embodiments of the present disclosure disclosed herein are not to be construed as limitations. Each group member may be referred to and claimed individually or in any combination with other members of the group or other elements found herein. One or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

What is claimed is:

1. A method for treating short stature or increasing a subject's height, comprising:
    administering a therapeutically effective amount of a FGFR inhibitor to a subject in need thereof wherein the FGFR inhibitor is erdafitinib.

2. The method of claim 1, further comprising selecting the subject in need of treating short stature or the subject in need of an increase in height before administering the FGFR inhibitor to the subject.

3. The method of claim 1, wherein the short stature is idiopathic short stature.

4. The method of claim 1, wherein the subject does not have a germline FGFR mutation.

5. The method of claim 1, wherein the subject has an open growth plate.

6. The method of claim 1, wherein the subject does not have cancer.

7. The method of claim 1, wherein the subject does not have a brain tumor.

8. The method of claim 1, wherein the subject is a pediatric subject.

9. The method of claim 1, wherein administering the FGFR inhibitor comprises administering the FGFR inhibitor once a day orally.

10. The method of claim 1, wherein administering the FGFR inhibitor comprises administering the FGFR inhibitor multiples times a day orally.

11. The method of claim 1, wherein the therapeutically effective amount of the FGFR inhibitor is between 4.2-5.2 mg/m$^2$ per day.

12. The method of claim 1, wherein the therapeutically effective amount of the FGFR inhibitor is about 4.7 mg/m$^2$ per day.

13. The method of claim 1, wherein the therapeutically effective amount of the FGFR inhibitor is less than 4.7 mg/m$^2$ per day.

14. The method of claim 1, wherein the therapeutically effective amount of the FGFR inhibitor is less than 4.2 mg/m$^2$ per day.

15. The method of claim 1, wherein the therapeutically effective amount of the FGFR inhibitor is less than 3.7, 3.2, 2.7, 2.2, 1.7, 1.2, 0.7, or 0.2 mg/m$^2$ per day.

16. The method of claim 1, wherein the therapeutically effective amount of the FGFR inhibitor is less than 4.0, 3.5, 3.0, 2.5, 2.0, 1.5, 1.0 or 0.5 mg/m$^2$ per day.

17. The method of claim 1, wherein administering the FGFR inhibitor comprises metronomic administration.

* * * * *